US009683249B2

(12) United States Patent
Medoff et al.

(10) Patent No.: US 9,683,249 B2
(45) Date of Patent: Jun. 20, 2017

(54) PROCESSING BIOMASS

(71) Applicant: Xyleco, Inc., Woburn, MA (US)

(72) Inventors: Marshall Medoff, Brookline, MA (US); Thomas Craig Masterman, Brookline, MA (US); James Lynch, Woburn, MA (US)

(73) Assignee: XYLECO, INC., Wakefield, MA (US)

( * ) Notice: Subject to any disclaimer, the term of this patent is extended or adjusted under 35 U.S.C. 154(b) by 85 days.

(21) Appl. No.: 14/016,461

(22) Filed: Sep. 3, 2013

(65) Prior Publication Data

US 2016/0076014 A1    Mar. 17, 2016

Related U.S. Application Data

(63) Continuation of application No. PCT/US2012/071092, filed on Dec. 20, 2012.

(60) Provisional application No. 61/579,550, filed on Dec. 22, 2011, provisional application No. 61/579,562, filed on Dec. 22, 2011.

(51) Int. Cl.
*C12P 19/14* (2006.01)
*C12P 7/10* (2006.01)
*C12N 9/42* (2006.01)
*C12P 5/02* (2006.01)
*C12P 7/04* (2006.01)
*C12P 7/16* (2006.01)
*C12P 7/24* (2006.01)
*C12P 7/28* (2006.01)
*C12P 7/40* (2006.01)
*C12P 7/42* (2006.01)
*C12P 7/46* (2006.01)
*C12P 7/48* (2006.01)
*C12P 7/52* (2006.01)
*C12P 7/56* (2006.01)
*C12P 7/62* (2006.01)
*C12P 19/02* (2006.01)
*C12P 19/04* (2006.01)
*C12P 19/12* (2006.01)

(52) U.S. Cl.
CPC ............ *C12P 19/14* (2013.01); *C12N 9/2434* (2013.01); *C12N 9/2437* (2013.01); *C12P 5/02* (2013.01); *C12P 5/023* (2013.01); *C12P 7/04* (2013.01); *C12P 7/10* (2013.01); *C12P 7/16* (2013.01); *C12P 7/24* (2013.01); *C12P 7/28* (2013.01); *C12P 7/40* (2013.01); *C12P 7/42* (2013.01); *C12P 7/46* (2013.01); *C12P 7/48* (2013.01); *C12P 7/52* (2013.01); *C12P 7/56* (2013.01); *C12P 7/62* (2013.01); *C12P 19/02* (2013.01); *C12P 19/04* (2013.01); *C12P 19/12* (2013.01); *C12Y 302/01004* (2013.01); *C12P 2201/00* (2013.01); *Y02E 50/16* (2013.01); *Y02E 50/17* (2013.01); *Y02E 50/343* (2013.01)

(58) Field of Classification Search
None
See application file for complete search history.

(56) References Cited

U.S. PATENT DOCUMENTS

| 4,091,116 | A | * | 5/1978 | Edwards | ............... | A23C 9/1206 |
| | | | | | | 426/42 |
| 5,916,780 | A | | 6/1999 | Foody et al. | | |
| 6,207,729 | B1 | | 3/2001 | Medoff et al. | | |
| 7,402,428 | B2 | | 7/2008 | Forster et al. | | |
| 2003/0217383 | A1 | | 11/2003 | Reuber et al. | | |
| 2008/0206862 | A1 | | 8/2008 | Asgari | | |
| 2008/0268446 | A1 | | 10/2008 | Steichen et al. | | |
| 2009/0286295 | A1 | | 11/2009 | Medoff et al. | | |
| 2010/0200806 | A1 | | 8/2010 | Medoff et al. | | |
| 2010/0216203 | A1 | | 8/2010 | Trent et al. | | |
| 2010/0229256 | A1 | | 9/2010 | Somleva et al. | | |
| 2011/0117453 | A1 | | 5/2011 | Tokita et al. | | |
| 2013/0040350 | A1 | * | 2/2013 | Studer | ..................... | C12P 19/02 |
| | | | | | | 435/135 |
| 2014/0011258 | A1 | * | 1/2014 | Medoff | ..................... | C12P 19/14 |
| | | | | | | 435/209 |

FOREIGN PATENT DOCUMENTS

| CH | EP 2377918 A1 * | 10/2011 | ............... C12P 19/02 |
| EP | 2377918 | 10/2011 | |
| WO | 2009155601 A2 | 12/2009 | |

OTHER PUBLICATIONS

Miller, C. "Freezing Corn on the Cob",<www.thefamilyhomestead.com/freezecornoncob.htm>, 2010 (accessed online Mar. 17, 2016), 10 pages.*
American Type Culture Collection (ATCC) "Trichoderma reesei RUT-C30 (ATCC® 56765™)" ATCC Product Sheet, 2016, 11 pages.*
Taherzadeh et al "Pretreatment of Lignocellulosic Wastes to Improve Ethanol and Biogas Production: A Review" Int. J. Molec. Sci.,2008, 9(9),pp. 1621-1651.*
Rios, G.M., et al "Progress in enzymatic membrane reactors—a review" J. Membrane Sci. 2004, 242, 189-196.*
Chinese Search Report, Corresponding Chinese Application No. 2012800628522, dated Dec. 31, 2015, 2 pages.
Office Action—Corresponding Japanese Application No. 2014-548922, dated Oct. 4, 2016, 3 pages.
Baucher et al., "Lignin:Genetic Engineering and Impact on Pulping," Crit. Rev. Biochem. Mol. Biol. 38:305-350 (2003).
Chen et al., "Lignin Modification Improves Fermentable Sugar Yields for Biofuel Production," Nat. Biotechnol. (2007) 25:759-61 (2007).

(Continued)

*Primary Examiner* — Chris R Tate
*Assistant Examiner* — Aaron J Kosar
(74) *Attorney, Agent, or Firm* — Leber IP Law

(57) ABSTRACT

Provided herein are methods for processing biomass materials that are disposed in one or more structures or carriers, e.g., a bag, a shell, a net, a membrane, a mesh or any combination of these. Containing the material in this manner allows it to be readily added or removed at any point and in any sequence during processing.

22 Claims, 3 Drawing Sheets

(56) References Cited

OTHER PUBLICATIONS

Kumar et al., "Methods for Pretreatment of Lignocellulosic Biomass for Efficient Hydrolysis and Biofuel Production," Ind. Eng. Chem. Res. 48:3713-29 (2009).

Seidl, V. et al., "The Hypocrea jecorina (Trichoderma reesei) hypercellulolytic mutant RUT C30 lacks a 85 kb (29 gene-encoding) region of the wild-type genome," BMC Genomics, vol. 9: 15 pages (2008).

Kurasawa, T. et al., "Induction of Cellulase by Gentiobiose and Its Sulfur-Containing Analog in Penicillium purpurogenum," Appl. Environ. Microbial., vol. 58(1): 106-110 (Jan. 1992).

Seidl, V. and Seiboth, B., "Trichoderma reesei: genetic approaches to improving strain efficiency," Biofuels, vol. 1(20: 343-354 (2010).

* cited by examiner

PROCESSING BIOMASS

CROSS REFERENCE TO RELATED APPLICATIONS

This application is a continuation of PCT/US2012/071092 filed Dec. 20, 2012, which claimed priority to U.S. Provisional Application Nos. 61/579,550 and 61/579,562, both filed on Dec. 22, 2011. The entire disclosures of the above applications are incorporated herein by reference.

FIELD OF THE INVENTION

The invention pertains to improvements in conducting microbiological, biological and biochemical reactions.

BACKGROUND

As demand for petroleum increases, so too does interest in renewable feedstocks for manufacturing biofuels and biochemicals. The use of lignocellulosic biomass as a feedstock for such manufacturing processes has been studied since the 1970s. Lignocellulosic biomass is attractive because it is abundant, renewable, domestically produced, and does not compete with food industry uses.

Many potential lignocellulosic feedstocks are available today, including agricultural residues, woody biomass, municipal waste, oilseeds/cakes and sea weeds, to name a few. At present these materials are either used as animal feed, biocompost materials, are burned in a cogeneration facility or are landfilled.

Lignocellulosic biomass is recalcitrant to degradation as the plant cell walls have a structure that is rigid and compact. The structure comprises crystalline cellulose fibrils embedded in a hemicellulose matrix, surrounded by lignin. This compact matrix is difficult to access by enzymes and other chemical, biochemical and biological processes. Cellulosic biomass materials (e.g., biomass material from which substantially all the lignin has been removed) can be more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

While a number of methods have been tried to extract structural carbohydrates from lignocellulosic biomass, they are either are too expensive, produce too low a yield, leave undesirable chemicals in the resulting product, or simply degrade the sugars.

Monosaccharides from renewable biomass sources could become the basis of the chemicals and fuels industries by replacing, supplementing or substituting petroleum and other fossil feedstocks. However, techniques need to be developed that will make these monosaccharides available in large quantities and at acceptable purities and prices.

SUMMARY OF THE INVENTION

Provided herein are methods for producing a product, where the method includes: providing a structure or carrier, wherein the structure or carrier possesses one or more pores configured to allow the passage of molecules; and disposing within the structure or carrier, a cellulosic or lignocellulosic biomass or an additive.

Also provided herein are methods for producing a product, where the method includes: providing a liquid medium; providing a cellulosic or lignocellulosic biomass; providing an additive; providing a structure or carrier, wherein the structure or carrier possesses one or more pores configured to allow the passage of molecules; disposing the cellulosic or lignocellulosic biomass or the additive, within the structure or carrier; combining the liquid medium, the structure or carrier, and either the additive or the cellulosic or lignocellulosic biomass to make a combination; maintaining the combination under conditions that allow the passage of molecules out of and/or into the structure or carrier; and maintaining the combination under conditions that allow the additive to convert the molecules to one or more products; thereby producing a product.

In another aspect, provided herein is a method for producing a product, where the method includes: providing a liquid medium; providing a cellulosic or lignocellulosic biomass, wherein the cellulosic or lignocellulosic biomass is disposed in a structure or carrier, and wherein the structure or carrier possesses one or more pores configured to allow the passage of molecules; providing an additive; combining the structure or carrier and the additive in the liquid medium to make a combination; maintaining the combination under conditions that allow the passage of molecules out of and/or into the structure or carrier; and maintaining the combination under conditions that allow the additive to convert the molecules to one or more products; thereby producing a product.

Additionally, provided herein are methods of producing an enzyme, where the methods include: providing a liquid medium; providing a cellulosic or lignocellulosic biomass; providing a microorganism capable of producing an enzyme in the presence of the cellulosic or lignocellulosic biomass; providing a structure or carrier, wherein the structure or carrier possesses one or more pores configured to allow the passage of molecules; disposing the cellulosic or lignocellulosic biomass within the structure or carrier; combining the liquid medium, the structure or carrier, and the microorganism to make a combination; and maintaining the combination under conditions that allow the microorganism to produce the enzyme; thereby producing an enzyme.

Also provided herein is a method of providing a substance to a microorganism, where the method includes: providing a liquid medium; providing a microorganism; providing a substance; providing a structure or carrier, wherein the structure or carrier possesses one or more pores configured to allow the passage of the substance into and out of the structure or carrier; either: by disposing the microorganism within the structure or carrier, and forming a combination by combining the liquid medium, the microorganism within the structure or carrier and the substance, or by disposing the substance within the structure or carrier, and forming a combination by combining the liquid medium, the substance within the structure or carrier, and the microorganism; and maintaining the combination under conditions that allow the substance to move out of and into the structure or carrier, and to come in contact with the microorganism; thereby providing the substance to the microorganism. Such methods can also include: providing a second structure or carrier; and disposing both the microorganism and the substance each in a separate structure or carrier.

Also provided herein is a method of making a product, where the method includes: providing a liquid medium; providing a microorganism; providing a substance; providing a structure or carrier, where the structure or carrier possesses one or more pores configured to allow the passage of the substance into and out of the structure or carrier; combining the liquid medium, the microorganism, and the substance in the container, thereby producing a combination; maintaining the combination under conditions where the substance is released into the liquid medium; and maintaining the combination under conditions where the microorganism makes the product; thereby providing the substance to the microorganism.

Also provided herein is a system for making a product, where the system includes: a liquid medium in a container; a microorganism capable of making a product; and a structure or carrier containing a substance, where the structure or carrier is configured to release the substance into the liquid medium.

In any of the methods or systems provided herein, the cellulosic or lignocellulosic biomass can be disposed within the structure or carrier, and the methods can further include: disposing the additive within a second structure or carrier; and the structure or carrier containing the cellulosic or lignocellulosic biomass is disposed within the second structure or carrier.

In any of the methods or systems provided herein, the substance can be a sugar, e.g., a sugar can be disposed within one or more structures or carriers.

In any of the methods or systems provided herein, the product produced can be a molecule, a protein, a sugar, a fuel or combinations thereof. The protein can be an enzyme.

Any of the methods or systems provided herein can further include disposing a microorganism in the structure or carrier. Alternatively, the cellulosic or lignocellulosic material, or the additive can be disposed in the structure or carrier. The cellulosic or lignocellulosic material, the additive, or the microorganism can be disposed in a second structure or carrier. The additive can be a microorganism, an enzyme, an acid, a base or combinations thereof.

In any of the methods or systems provided herein, the structure or carrier can be a bag, a shell, a net, a membrane, a mesh or combinations thereof. Where the structure or carrier includes a bag, the bag can be formed of a mesh material having a maximum opening size of less than 1 mm. Alternatively, the mesh material can have an average pore size of from about 10 mm to 1 nm. Where the structure or carrier is a bag, the bag can be made of a bioerodible polymer. The bioerodible polymer can be selected from the group consisting of: polylactic acid, polyhydroxybutyrate, polyhydroxyalkanoate, polyhydroxybutyrate-valerate, polycaprolactone, polyhydroxybutyrate-hexanoate, polybutylene succinate, polybutyrate succinate adipate, polyesteramide, polybutylene adipate-co-terephthalate, mixtures thereof, and laminates thereof. The bag can be made of a starch film.

In any of the methods or systems provided herein, the combination can be placed in a fermentation vessel that includes impellers, and where the combination is maintained under conditions where the bag is torn open by the impellers.

In any of the methods or systems provided herein, the microorganism or microorganisms can include a strain of *Trichoderma reesei*, e.g., a high-yielding cellulase-producing mutant of *Trichoderma reesei*, e.g., the RUT-C30 strain.

In any of the methods or systems provided herein, the recalcitrance of the cellulosic or lignocellulosic material can have been reduced relative to the material in its native state. Such treatment to reduce recalcitrance can be bombardment with electrons, sonication, oxidation, pyrolysis, steam explosion, chemical treatment, mechanical treatment, freeze grinding, or combinations of such treatments. Preferably, the recalcitrance of the cellulosic or lignocellulosic biomass has been reduced by exposure to an electron beam.

In any of the methods or systems provided, the conversion can be saccharification, and the product can be a sugar solution or suspension. The methods can further include isolating a sugar from the sugar solution or suspension. The sugar isolated can be xylose.

In any of the systems or methods provided herein, the cellulosic or lignocellulosic biomass can be: paper, paper products, paper waste, paper pulp, pigmented papers, loaded papers, coated papers, filled papers, magazines, printed matter, printer paper, polycoated paper, card stock, cardboard, paperboard, cotton, wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, offal, arracacha, buckwheat, banana, barley, cassava, kudzu, oca, sago, sorghum, potato, sweet potato, taro, yams, beans, favas, lentils, peas, or mixtures of any of these. The cellulosic or lignocellulosic material can include corn cobs. The cellulosic or lignocellulosic biomass can be comminuted, e.g., by dry milling, or by wet milling. The cellulosic or lignocellulosic material can be treated to reduce its bulk density, or to increase its surface area. The cellulosic or lignocellulosic material can have an average particle size of less than about 1 mm, or an average particle size of from about 0.25 mm to 2.5 mm.

It should be understood that this invention is not limited to the embodiments disclosed in this Summary, and it is intended to cover modifications that are within the spirit and scope of the invention, as defined by the claims.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

Figure 1:
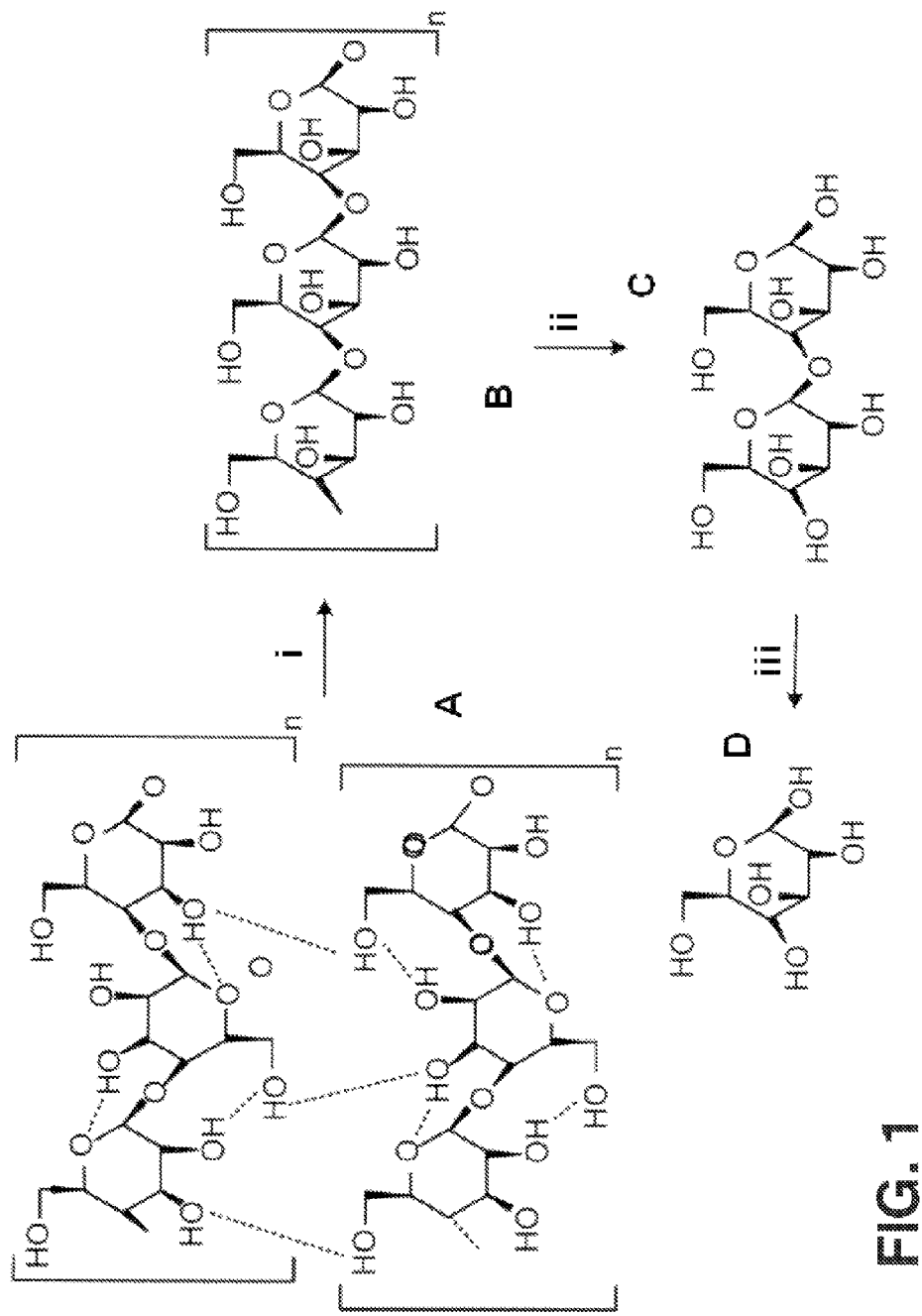
FIG. 1 is a diagram illustrating the enzymatic hydrolysis of cellulose to glucose. Cellulosic substrate (A) is converted by endocellulase (i) to cellulose (B), which is converted by exocellulase (ii) to cellobiose (C), which is converted to glucose (D) by cellobiase (beta-glucosidase) (iii).

Provided herein are methods of conducting biological, microbiological, and biochemical reactions by using one or more structures or containers, which can have pores or other openings, or can be degradable. The structure can be a bag, net or mesh, shell (e.g., rigid or semi-rigid shell), a membrane, or combinations of these structures (e.g., one or more structures of one or more types can be disposed within a structure of the same or another type). The structures can hold various parts or ingredients involved in biological, microbiological, and biochemical reactions. Containing the material in this manner allows parts or ingredients, e.g., biomass, such as treated biomass, to be readily added or removed at any point and in any sequence during such reactions. The invention also allows simplification of purification of products (such as e.g., sugars or other products of saccharification or fermentation), and can aid in the maintenance of the level of a metabolite, sugar, or nutrient.

For instance, the structures can be used to provide one or more nutrients to microorganisms. The nutrients can be placed in the structure, and the structure placed in a liquid medium containing microorganisms. The nutrients are released from the structure into the medium to be accessed by the microorganisms. Alternatively, the microorganisms can be placed within the structure, and the structure placed in a liquid medium that contains the nutrients.

In a preferred embodiment, the structure can contain biomass which is to be acted on by microorganisms, or products of microorganisms, such as enzymes or signal molecules. For instance, the biomass can be placed in the structure, which is then placed in a liquid medium with the microorganisms. Substances from the biomass are able to leach out of the structure and be accessed by the microorganisms and enzymes secreted by the microorganisms, and enzymes produced by the microorganisms can migrate into the structures and act on the biomass.

In another aspect, the invention relates to producing enzymes using a microorganism in the presence of a biomass material. The biomass material acts in the enzyme production process as an inducer for cellulase synthesis, producing a cellulase complex having an activity that is tailored to the particular biomass material, which in some implementations is the same material that is to be saccharified by the cellulase complex.

The invention also features a method that includes contacting a cellulosic or lignocellulosic material disposed in a structure or carrier, in a medium, with an additive to produce a product. The additive can, for example, be a microorganism, an enzyme, an acid, a base or mixtures of any of these. The additives can be added in any order. The product can be, for example, a molecule, a protein, a sugar, a fuel or mixtures of any of these. The products can be produced in any order. For example, a protein can be first produced, followed by a sugar and finally by a fuel. Optionally, the protein can be an enzyme.

The migration of substances into and out of the structure can be accomplished in a variety of ways. The structure can slowly degrade over time in the medium, the structure can be made of a porous material that releases the nutrients into the medium, the structure can be made of a material that is consumed by the microorganisms, the structure can be made of a material that is torn open by the impellers in the bottom of a fermentation vessel, or the structure can be made of a material that swells and bursts in the medium.

In an embodiment of the process described herein, a biomass can be disposed in, on, or placed into the structure or carrier. The biomass can be treated before or after being placed into the structure or carrier. Additives, nutrients and products can also be disposed in the structure or carrier with or without the biomass. For example, a biomass with an antibiotic, a microbe, an enzyme and a sugar can be disposed in the structure, and may be combined in any amounts and in any sequence during the process.

Optionally, the biomass can be outside of the structure or carrier. For example, a microbe can be disposed in, within (i.e., built into the structure or carrier), or on the structure or carrier, which is contacted with a medium containing the biomass. As another example, there may be one kind of biomass in the structure or carrier and a second kind of biomass outside the structure or carrier. There may be multiple biomasses inside and outside of the structure or carrier added in any combination and sequence during the process.

In another embodiment of the process, there may be multiple structures or carriers placed in or contacted with a medium. These can be placed in the medium in any sequence and combination during the process. The structure or carriers can be, for example, with respect to each other made of the same material or different materials, have the same shape or different shapes, and may be used in any combination.

For example, multiple structures or carriers can be disposed within another structure or carrier. The various structures or carriers can be of the same type, or can be of different types. Multiple structures or carriers can be sequentially disposed, each inside another, e.g., similar to "nesting dolls."

For example, it may be convenient to have biomaterial disposed in a plurality of structures or carriers of a uniform size and volume, each containing the same or a similar amount of biomass. In this way, whole number amounts or units of the structure or carrier can be contacted with the medium, with the number of units used depending on the batch size in the process. Such uniform volume structures or carriers may also be more convenient to store, for example, if they are designed as approximately cuboid in shape so that they can be easily stacked.

Optionally, in some implementations, a structure or carrier containing biomass can be contacted with a medium in combination with a structure or carrier that is designed to slowly release an additive, e.g., an enzyme, contained within the structure or carrier. For example, controlled release may be effected by having a controlled pore size (e.g., a pore size smaller than 10 um, e.g., smaller than 1 um, smaller than 0.1 um).

As another example, one or more biomass-containing structures or carriers, and one or more microbe-containing structures or carriers can be contacted simultaneously or sequentially with a medium.

As a further example, in some processes one or more biomass-containing structures or carriers, and one or more additive-containing water-degradable structures or carriers are contacted with an aqueous medium.

In another embodiment of the process, the structure or carrier can be removed at any point in the process and in any sequence. For example, the structure or carrier including its contents can be removed after producing a product, and/or additional structures or carriers including their contents can be added during production of a product.

As another example, a biomass disposed in a structure or carrier is contacted with an aqueous medium, and a microbe is added to the aqueous medium, which then produces a product. Subsequently, the biomass-containing structure or carrier can be removed, and a second amount of biomass in a structure or carrier can be added to produce more product. Optionally, the microbe can be removed before or after addition of the second biomass.

In yet another example, a biomass can be disposed in a structure or carrier and contacted with an aqueous medium containing a microbe the combination of which produces a first product. The microbe can be optionally removed (e.g., by filtration or centrifugation) or killed (e.g., by application of antibiotics, heat, or ultraviolet light) and subsequently a different microbe can be added, which causes a second product to be produced.

In a further example, a biomass can be disposed in a first structure or carrier. The first structure or carrier can be disposed in a second structure or carrier containing a microbe. The two structures or carriers can be disposed in a medium. The second structure or carrier is designed to contain the microbes (e.g., has pore sizes below about 5 um, below about 1 um, below about 0.4 um, below about 0.2 um). The combination produces a product that optionally can flow out of the second structure or carrier. Once product is produced, the first and second structures and contents can be removed leaving media with product dispersed and/or dissolved within it. The combination of the first and second structures or carriers with their contents can be optionally used in another medium to produce more product.

The processes described herein include processing of biomass and biomass materials and the intermediates and products resulting from such processing. During at least a part of the processing, the biomass material can be disposed in a structure or carrier.

The processes described herein include producing enzymes using a microorganism in the presence of a biomass material, e.g., a cellulosic or lignocellulosic material. Enzymes made by the processes described herein contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

As shown in FIG. 1, for example, during saccharification a cellulosic substrate (A) is initially hydrolyzed by endoglucanases (i) at random locations producing oligomeric intermediates (e.g., cellulose) (B). These intermediates are then substrates for exo-splitting glucanases (ii) such as cellobiohydrolase to produce cellobiose from the ends of the cellulose polymer. Cellobiose is a water-soluble 1,4-linked dimer of glucose. Finally, cellobiase (iii) cleaves cellobiose (C) to yield glucose (D). Therefore, the endoglucanases are particularly effective in attacking the crystalline portions of cellulose and increasing the effectiveness of exocellulases to produce cellobiose, which then requires the specificity of the cellobiose to produce glucose. Therefore, it is evident that depending on the nature and structure of the cellulosic substrate, the amount and type of the three different enzymes may need to be modified.

In some implementations, the enzyme is produced by a fungus, e.g., by strains of the cellulolytic filamentous fungus *Trichoderma reesei*. For example, high-yielding cellulase mutants of *Trichoderma reesei* may be used, e.g., RUT-NG14, PC3-7, QM9414 and/or Rut-C30. Such strains are described, for example, in "Selective Screening Methods for the Isolation of High Yielding Cellulase Mutants of *Trichoderma reesei*," Montenecourt, B. S. and Everleigh, D. E., *Adv. Chem. Ser.* 181, 289-301 (1979), the full disclosure of which is incorporated herein by reference. Other cellulase-producing microorganisms may also be used.

As will be discussed further below, once the enzyme has been produced, it can be used to saccharify biomass, in some cases the same type of biomass material that has been used to produce the enzyme. The process for converting the biomass material to a desired product or intermediate generally includes other steps in addition to this saccharification step. Such steps are described, e.g., in U.S. Pat. App. Pub. 2012/0100577 A1, filed Oct. 18, 2011 and published Apr. 26, 2012, the full disclosure of which is hereby incorporated herein by reference.

Figure 2:
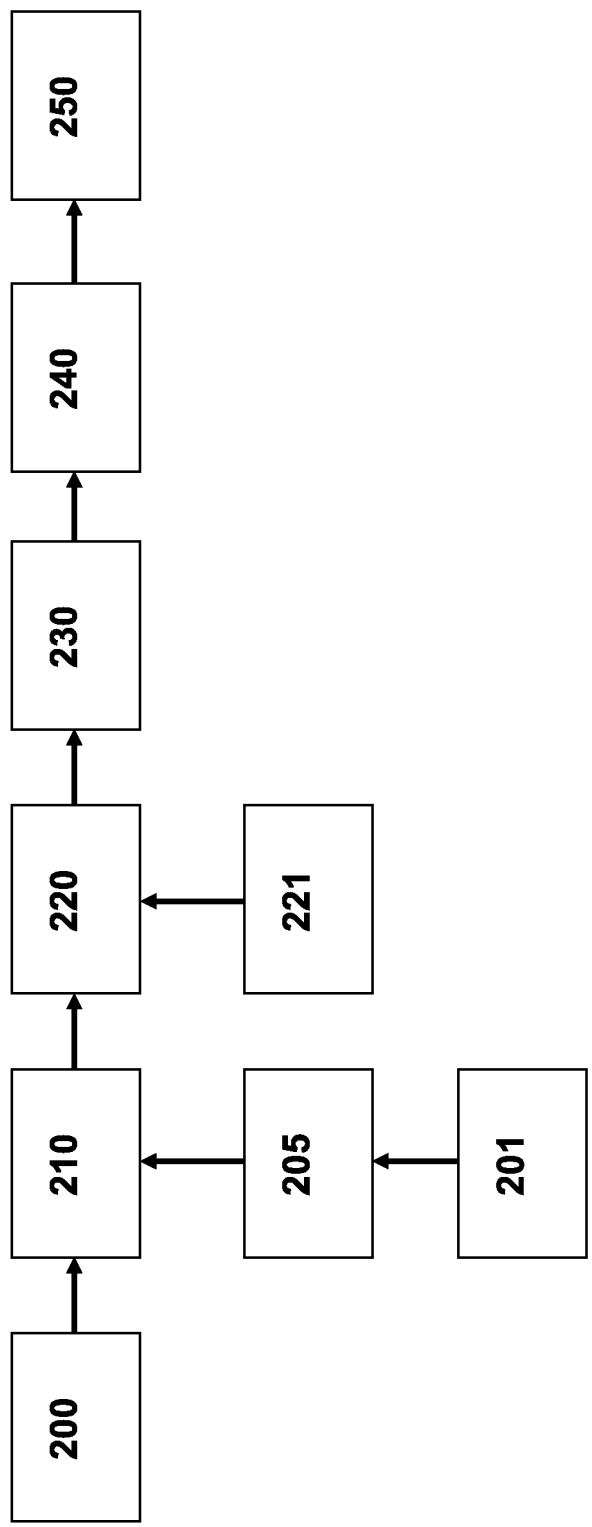
FIG. 2 is a flow diagram illustrating conversion of a biomass feedstock to one or more products. Feedstock is physically pretreated (e.g., to reduce its size) (200), optionally treated to reduce its recalcitrance (210), saccharified to form a sugar solution (220), the solution is transported (230) to a manufacturing plant (e.g., by pipeline, railcar) (or if saccharification is performed en route, the feedstock, enzyme and water is transported), the saccharified feedstock is bio-processed to produce a desired product (e.g., alcohol) (240), and the product can be processed further, e.g., by distillation, to produce a final product (250). Treatment for recalcitrance can be modified by measuring lignin content (201) and setting or adjusting process parameters (205). Saccharifying the feedstock (220) can be modified by mixing the feedstock with medium and the enzyme (221).

For example, referring to FIG. 2, a process for manufacturing an alcohol can include, for example, optionally mechanically treating a feedstock, e.g., to reduce its size (200), before and/or after this treatment, optionally treating the feedstock with another physical treatment to further reduce its recalcitrance (210), then saccharifying the feedstock, using the enzyme complex, to form a sugar solution (220). Optionally, the method may also include transporting, e.g., by pipeline, railcar, truck or barge, the solution (or the feedstock, enzyme and water, if saccharification is performed en route) to a manufacturing plant (230). In some cases the saccharified feedstock is further bioprocessed (e.g., fermented) to produce a desired product e.g., alcohol (240). This resulting product may in some implementations be processed further, e.g., by distillation (250), to produce a final product. One method of reducing the recalcitrance of the feedstock is by electron bombardment of the feedstock. If desired, the steps of measuring lignin content of the feedstock (201) and setting or adjusting process parameters based on this measurement (205) can be performed at various stages of the process, as described in U.S. Pat. App. Pub. 2010/0203495 A1 by Medoff and Masterman, published Aug. 12, 2010, the complete disclosure of which is incorporated herein by reference. Saccharifying the feedstock (220) can also be modified by mixing the feedstock with medium and the enzyme (221).

Figure 3:
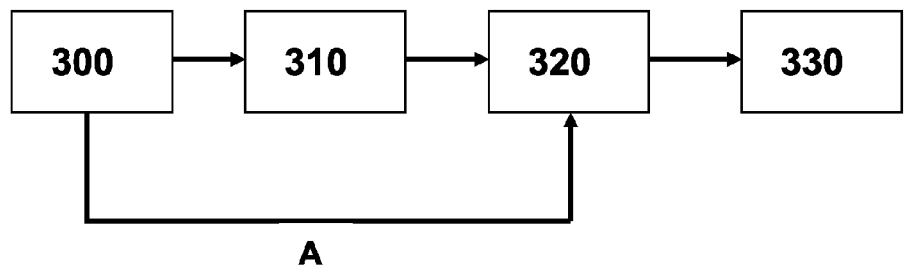
FIG. 3 is a flow diagram illustrating the treatment of a first biomass (300), addition of a cellulase producing organism (310), addition of a second biomass (320), and processing the resulting sugars to make products (e.g., alcohol(s), pure sugars) (330). The first treated biomass can optionally be split, and a portion added as the second biomass (A).

For example, referring to FIG. 3, a first biomass is optionally treated (300), for example, to reduce its size and/or recalcitrance, and placed into a structure or carrier. Optionally, the first biomass can first be placed into a first structure or carrier and then treated. The biomass containing structure or carrier is then contacted with an aqueous medium and a cellulase producing organism (310). After an adequate time has passed for the cells to grow to a desired stage and enough enzymes have been produced, a second biomass, optionally disposed in a second structure or carrier, may be added (320). Optionally, the structure or carrier containing the first biomass can be removed prior to or at any point after addition of the second biomass. The action of the enzyme on the second and any remaining first biomass produces mixed sugars which can be further processed to useful products (330). Optionally, the second structure or carrier containing the second biomass can be removed prior to or after the production of the useful product. The first and second biomass can be portions of the same biomass material. For example, a portion of the biomass can be placed into a structure or carrier and contacted with a medium containing the cellulase producing organism. Once some enzymes have been produced; the enzyme containing media can be combined with the second biomass (A). Optionally, the first and second biomass may be pretreated to reduce recalcitrance. The first and second biomass can also be contained in a single structure or carrier. The structure or carrier can form a liner for a bioreactor. Multiple biomass containing structures or carriers can also be used. The aqueous media will be discussed below. In some cases, rather than adding the second biomass to the reactor, the enzyme is harvested, stored, and used in a later saccharification process.

Figure 4:
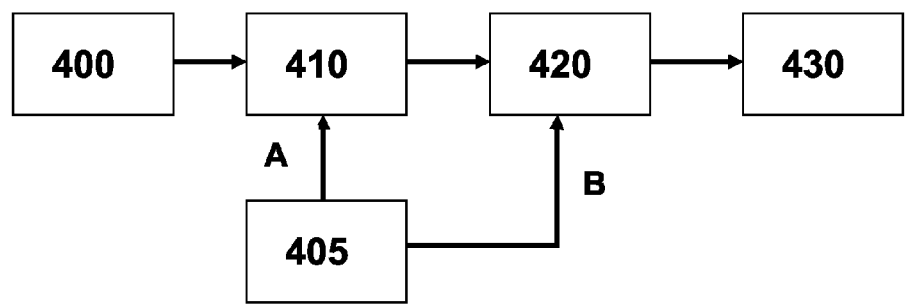
FIG. 4 is a flow diagram illustrating the production of enzymes. A cellulase-producing organism is added to growth medium (400), a treated first biomass (405) is added (A) to make a mixture (410), a second biomass portion is added (420), and the resulting sugars are processed to make products (e.g., alcohol(s), pure sugars) (430). Portions of the first biomass (405) can also be added (B) to the second biomass (420).

Referring now to FIG. 4, the cellulase-producing organism (400) can be grown in a growth medium for a time to reach a specific growth phase. For example, this growth period could extend over a period of days or even weeks. Pretreated first biomass (405) is placed in a structure or carrier and can then be contacted with the enzyme producing cells (410) so that after a time enzymes are produced. Enzyme production may also take place over an extended period of time. The enzyme containing solution may then be combined with a second biomass (420). Optionally, before addition of the second biomass or at any point after addition of the second biomass, the structure or carrier containing the first biomass can be removed. The action of the enzyme on the second and remaining first biomass produces mixed sugars which can be further processed to useful products (430). The first and second biomass can be portions of the same biomass or can be similar but not identical (e.g., pretreated and non-pretreated) material (B). Again, if desired, the enzyme can be harvested and stored rather than being used immediately with a second biomass.

Along with the methods discussed above, the cellulose producing organism may be harvested prior to being combined with the first pretreated biomass. Harvesting may include partial or almost complete removal of the solvent and growth media components. For example, the cells may be collected by centrifugation and then washed with water or another solution.

In another embodiment, after enzyme is produced, the structure or carrier can be removed from the enzyme-containing medium and the enzyme can be concentrated. Concentration may be by any useful method including chromatography, centrifugation, filtration, dialysis, extraction, evaporation of solvents, spray drying and adsorption onto a solid support. The concentrated enzyme can be stored for a time and then be used by addition to a second biomass to produce useful products.

In another implementation of the method, the enzyme is produced by the selected microorganism in a liquid (e.g., aqueous) medium, in the presence of the biomass material. In order to contain the biomass material within the medium, the biomass material is disposed in a structure or carrier, for example a mesh bag or other porous container with openings or pores. The pore size is such that preferably at least 80% (more preferably at least 90%, at least 95% or at least 99%) of the insoluble portion of the biomass material is retained within the structure or carrier during enzyme production. For instance, at least 80%, 81%, 82%, 83%, 84%, 85%, 86%, 87%, 88%, 89%, 90%, 91%, 92%, 93%, 94%, 95%, 96%, 97%, 98%, 99% of the insoluble portion of the biomass material is retained within the structure or carrier during enzyme production.

It is preferred that the pore size or mesh size of the container be such that substantially none of the insoluble portion of the biomass material flows out of the container during enzyme production. It is also preferred that the pore size be large enough to allow molecules such as sugars, soluble polysaccharides, proteins and biomolecules to pass. Preferably the pore size is large enough that large molecules such as proteins do not foul or block the pores during the course of enzyme production.

Thus, it is generally preferred that the nominal pore size or mesh size be smaller than most of all of the particles of the biomass material. In some implementations the absolute pore size is smaller than 50% (preferably smaller than 60%, 70%, 80%, 90%, 95%, 98% or 99%) of the particles of the biomass material. For instance, the absolute pore size can be smaller that 50%, 51%, 52%, 53%, 54%, 55%, 56%, 57%, 58%, or 59% of the particles of the biomass material. Preferably the absolute pore size can be smaller than 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% of the particles of the biomass material.

The aqueous media used in the above described methods can contain added yeast extract, corn steep, peptones, amino acids, ammonium salts, phosphate salts, potassium salts, magnesium salts, calcium salts, iron salts, manganese salts, zinc salts and cobalt salts. In addition to these components, the growth media typically contains 0 to 10% glucose (e.g., 1 to 5% glucose) as a carbon source. The inducer media can contain, in addition to the biomass discussed previously, other inducers. For example, some known inducers are lactose, pure cellulose and sophorose. Various components can be added and removed during the processing to optimize the desired production of useful products.

The concentration of the biomass typically used for inducing enzyme production is greater than 0.1 wt % (e.g., greater than or equal to 1%) and less than or equal to 50 wt % (less than or equal to 40 wt %, less than or equal to 30 wt %, less than or equal to 20 wt %, less than or equal to 10 wt %, less than or equal to 5 wt %). For instance, the concentration of biomass used for enzyme induction can be 0.1 wt %, 0.2, 0.3, 0.4, 0.5, 0.6, 0.7, 0.8, 0.9, or 1.0 wt %. The concentration of biomass can be 2, 3, 4, 5, 6, 7, 8, 9, or 10 wt %. The concentration of biomass can be 15, 20, 25, 30, 35, 40, 45, or 50 wt %.

Any of the processes described herein may be performed as a batch, a fed-batch or a continuous process. The processes are especially useful for industrial scale production, e.g., having a culture medium of at least 50 liters, preferably at least 100 liters, more preferably at least 500 liters, even more preferably at least 1,000 liters, in particular at least 5,000 liters or 50,000 liters or 500,000 liters. The process may be carried out aerobically or anaerobically. Some enzymes are produced by submerged cultivation and some by surface cultivation.

In any of the process described herein, the enzyme can be manufactured and stored and then used to in saccharification reactions at a later date and/or in a different location.

Any of the processes described herein may be conducted with agitation. In some cases, agitation may be performed using jet mixing as described in U.S. Pat. App. Pub. 2010/0297705 A1, filed May 18, 2010 and published on Nov. 25, 2012, U.S. Pat. App. Pub. 2012/0100572 A1, filed Nov. 10, 2011 and published on Apr. 26, 2012, U.S. Pat. App. Pub. 2012/0091035 A1, filed Nov. 10, 2011 and published on Apr. 19, 2012, the full disclosures of which are incorporated by reference herein.

Temperatures for the growth of enzyme-producing organisms are chosen to enhance organism growth. For example, for *Trichoderma reesei*, the optimal temperature is generally between 20 and 40° C. (e.g., 30° C.), and the temperature for enzyme production can be optimized for that part of the process. For example, for *Trichoderma reesei* the optimal temperature for enzyme production is between 20 and 40° C. (e.g., 27° C.).

Structure or Carrier

The structure or carrier can be, for example, a bag, net, membrane, shell or combinations of any of these.

The structure or carrier can be made with a thermoplastic resin, for example, polyethylene, polypropylene, polystyrene, polycarbonate, polybutylene, a thermoplastic polyester, a polyether, a thermoplastic polyurethane, polyvinylchloride, polyvinylidene difluoride, a polyamide or any combination of these.

The structure or carrier can also be made of woven or non-woven fibers. Some preferred synthetic fiber or non-fiber materials are, for example, polyester, aramid, polyolefin, PTFE, polyphenlene sulfide, polyurethane, polyimide, acrylic, nylon and any combination of these.

The structure of carrier can also be made from biodegradable and/or water soluble polymers, for example, aliphatic polyesters, polyhydroxyalkanoates (PHAs), poly-3-hydroxybutyrate, polyhydroxyvalerate, polyhydroxyhexanoate, polylactic acid, polybutylene succinate, polybutylene succinate adipate, polycaprolactone, polyvinyl alcohol, polyanhydrides, starch derivatives, cellulose esters, cellulose acetate, nitrocellulose and any combination of these.

Other materials contemplated for the structure or carrier include, for example, metal (e.g., aluminum, copper), an alloy (e.g., brass, stainless steel), a ceramic (e.g., glass, alumina), a thermosetting polymer (e.g., bakelite), a composite material (e.g., fiberglass), a biopolymer and any combination of these. Any structural material, for example, as disclosed above, can be combined to provide the structure or carrier.

The structure or carrier can be made of a biodegradable, bioerodible, and/or water soluble polymer. Such a polymer can be chosen to degrade and release the material within it at or near a designated time. The polymer can be selected so that it will serve as a carbon source or nutritive source for the microorganisms being cultured. Polyhydroxyalkanoates, for instance, are readily consumed by many composting fungi and bacteria. PHAs can be a good choice for a structure or carrier designed to release its contents into a culture of such organisms.

Alternatively, the structure or carrier can be configured and made from materials intended to be torn apart by the impellers of a fermentation system. The fermentation mixing cycle can be scheduled to maintain the structure or carrier in an intact state for a period of time, and then altered to cause the structure or carrier to come in contact with the impellers.

The container or carrier can be of any suitable shape, for example, a toroid, sphere, cube, oval, cuboid, dog bone, cylindrical, hexagonal prism, cone, square based pyramid, envelope or combinations of these.

The container or structure can have a sealable and, in some cases, resealable opening such as a zipper, VELCRO™ hook and loop fastener, heat seal, clips, pressure sensitive adhesive, buttons or tie (e.g., with a string or drawstring).

The structure or container may be rigid, semi-rigid or non-rigid. A non-rigid container is expected to be generally flexible in most directions. A semi-rigid container can be expected to be somewhat flexible in most directions. In some implementations, the container comprises a flexible, fabric bag.

The bag may have some rigid components such as a frame made of a metal wire or rigid polymer. The container or carrier can have a surface texturing, for example, grooves, corrugation, and quilting.

The container can have partitions, for example, it can have different pouches made with the same or different materials and/or there may be two or more structures or carriers nested within each other.

The container or carrier may be designed so as to float on top of the medium or be partially submerged therein, or it may be designed to be fully submerged in the medium. For example, the bag may have hooks, loops or adhesives to allow it to attach to the wall of a bioreactor, tank or other container. It may also have weights to hold part or all of it submerged in the medium, and/or buoyant parts to keep parts of it above the medium. The container or carrier can be designed to be free in the medium.

The structures or carriers can have pores. With respect to pore size, it is known that permeable materials may contain a distribution of pore sizes. Typically the pore size is rated as absolute or nominal. An absolute pore size rating specifies the pore size at which a challenge material or organism of a particular size will be retained with 100% efficiency. A nominal pore size describes the ability of the permeable material to retain the majority of the particulates (e.g., 60 to 98%). Both ratings depend on process conditions such as the differential pressure, the temperature or the concentration.

In some implementations, the container has a nominal pore size or mesh size of less than about 10 mm, e.g., less than 1000 um, 750 um, 500 um, 250 um, 100 um, 75 um, 50 um, 25 um, 10 um, 1 um, 0.1 um, 10 nm or even less than 1 nm. In some implementations, the container has a nominal pore size or mesh larger than 1 nm, e.g., larger than 10 nm, 0.1 um, 10 um, 25 um, 50 um, 75 um, 100 um, 250 um, 500 um, 750 um, 1 mm or even 10 mm.

If the structure or carrier is made of a polymer, the pores may be formed by stretching the polymer, either uniaxially or biaxially. Such methods for formulating and stretching polymers to make films with a particular pore size are known in the art.

The structure or carrier may be designed to allow for the insertion of, for example, a mixing device, a monitoring device, a sampling device or combinations of any of these. The design may include, for example a sealable opening or fitting configured to receive such a device. The monitoring device can be, for example, a pH probe, an oxygen probe, a temperature probe, a chemical probe or any combinations of these. Optionally, the monitoring device can be remotely operated (e.g., by a wireless connection) and can be free or attached to the structure. The carrier or structure can have a tagging device, for example, a tag with an identifying alphanumerical label or identifying color.

In some implementations, it is preferred that the structure or carrier have sufficient surface area, for example, to allow good exchange between the contents of the structure or carrier and the medium or other external components, for example, between the additive and the biomass material. It can also be advantageous to have a high surface area to present a large area to which a microorganism, e.g., a cellulase-producing organism, can optionally attach.

Medium

In the methods described herein, the structure or carrier is contacted or placed in a medium. The medium can be, for example, a liquid, a gas, a chemical solution, a suspension, a colloid, an emulsion, a non-homogenous multiphase system (e.g., a hydrophilic phase layered with a hydrophobic phase) and any combinations of these. The medium can be further manipulated during or after the process; for example, it can be purified and reused by, for example, by filtration, centrifugation and/or irradiation. Optionally, the medium can contain, for example, nutrients, particulates (e.g., inorganic or organic containing), oligomers (e.g., viscosity modifiers), carbon sources, surfactants (e.g., anti-foam agents), lipids, fats, extracts (e.g., yeast extract, casein extracts and or vegetable extracts), metal ions (e.g., $Fe^{2+}$, $Mg^{2+}$, $Mn^{2+}$, $Cu^{2+}$, $Na^{1+}$, $Ca^{2+}$, $K^{1+}$), anions, nitrogen sources (e.g., amino acids, ammonia, urea), vitamins, proteins (e.g., peptones, enzymes), buffers (e.g., phosphates) added in any combination and sequence.

Additives

Additives used in the processes disclosed herein can include, by way of example, a microorganism, a nutrient, a spore, an enzyme, an acid, a base, a gas, an antibiotic, a pharmaceutical and any combination of these. The additives can be added in any sequence and combination during the process. The additives can be disposed in a structure or carrier or out of the structure or carrier in any combination or sequence.

Enzymes

In one embodiment of the process, the additive is an enzyme produced by filamentous fungi or bacteria.

Enzymes are produced by a wide variety of fungi, bacteria, yeasts, and other microorganisms, and there are many methods for optimizing the production and use of cellulases.

Filamentous fungi, or bacteria that produce cellulase, typically require a carbon source and an inducer for production of cellulase. In prior art processes the carbon source is typically glucose and the inducer is typically pure cellulose. Apart from the cost of pure glucose and pure cellulose, the secreted enzyme produced by this method can be inferior for saccharifying biomass. Without being bound by any specific theory, it is believed that the reason for this is that the enzymes produced are particularly suited for saccharification of the substrate used for inducing its production, and thus if the inducer is cellulose the enzymes may not be well suited for degrading lignocellulosic material.

The cellulase-producing organism's growth rate and state is determined by particular growth conditions. When the host cell culture is introduced into the fermentation medium, containing a carbon source, the inoculated culture passes through a number of stages. Initially growth does not occur. This period is referred to as the lag phase and may be considered a period of adaptation. During the next phase referred to as the "exponential phase" the growth rate of the host cell culture gradually increases and the carbon source is consumed. After a period of maximum growth, the rate ceases and the culture enters stationary phase. After a further period of time, the culture enters the death phase and the number of viable cells declines. Where in the growth phase the cellulase is expressed depends on the cellulase and host cell. For example, the cellulase may be expressed in the exponential phase, in the transient phase between the exponential phase and the stationary phase, or alternatively in the stationary phase and/or just before sporulation. The cellulase may also be produced in more than one of the above mentioned phases.

When contacted with a biomass, the cellulase producing organism will tend to produce enzymes that release molecules advantageous to the organism's growth, such as glucose. This is done through the phenomenon of enzyme induction. Since there are a variety of substrates in a particular biomaterial, there are a variety of cellulases, for example, the endoglucanase, exoglucanase and cellobiase discussed previously. By selecting a particular lignocellulosic material as the inducer, the relative concentrations and/or activities of these enzymes can be modulated so that the resulting enzyme complex will work efficiently on the lignocellulosic material used as the inducer or a similar material. For example, a biomaterial with a higher portion of crystalline cellulose may induce a more effective or higher amount of endoglucanase than a biomaterial with little crystalline cellulose.

Since cellulose is insoluble and impermeable to organisms, it has been suggested that when cellulose is used as an inducer, a soluble oligosaccharide(s) such as cellobiose is actually the direct inducer of cellulase. Expression at a basal level allows a small amount of cellulase to hydrolyze cellulose to soluble oligosaccharides or to an inducer. Once the inducer enters the cell, it triggers full-scale transcription of the cellulase gene mediated by activator proteins and activating elements. After cellulose is degraded a large amount of glucose is liberated, which causes catabolite repression.

Lignocellulosic materials comprise different combinations of cellulose, hemicellulose and lignin. Cellulose is a linear polymer of glucose forming a fairly stiff linear structure without significant coiling. Due to this structure and the disposition of hydroxyl groups that can hydrogen bond, cellulose contains crystalline and non-crystalline portions. The crystalline portions can also be of different types, noted as I (alpha) and I (beta), for example, depending on the location of hydrogen bonds between strands. The polymer lengths themselves can vary lending more variety to the form of the cellulose. Hemicellulose is any of several heteropolymers, such as xylan, glucuronoxylan, arabinoxylans, and xyloglucan. The primary sugar monomer present is xylose, although other monomers such as mannose, galactose, rhamnose, arabinose and glucose are present. Typically, hemicellulose forms branched structures with lower molecular weights than cellulose. Hemicellulose is therefore an amorphous material that is generally susceptible to enzymatic hydrolysis. Lignin is a complex high molecular weight heteropolymer generally. Although all lignins show variation in their composition, they have been described as an amorphous dendritic network polymer of phenyl propene units. The amounts of cellulose, hemicellulose and lignin in a specific biomaterial depends on the source of the biomaterial. For example, wood derived biomaterial can be about 38-49% cellulose, 7-26% hemicellulose and 23-34% lignin depending on the type. Grasses typically are 33-38% cellulose, 24-32% hemicellulose and 17-22% lignin. Clearly lignocellulosic biomass constitutes a large class of substrates.

The diversity of biomass materials may be further increased by pretreatment, for example, by changing the crystallinity and molecular weights of the polymers. The variation in the composition of the biomass may also increase due to geographical and seasonal variation, i.e., where and when the material was collected.

One of ordinary skill in the art can optimize the production of enzymes by microorganisms by adding yeast extract, corn steep, peptones, amino acids, ammonium salts, phosphate salts, potassium salts, magnesium salts, calcium salts, iron salts, manganese salts, zinc salts, cobalt salts, or other additives and/or nutrients and/or carbon sources. Various components can be added and removed during the processing to optimize the desired production of useful products.

Temperature, pH and other conditions optimal for growth of microorganisms and production of enzymes are generally known in the art.

Biomass Materials

As used herein, the term "biomass materials" includes lignocellulosic, cellulosic, starchy, and microbial materials.

Lignocellulosic materials include, but are not limited to, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), algae, seaweed, manure, sewage, and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases even the root system of the plant.

Advantageously, no additional nutrients (other than a nitrogen source, e.g., urea or ammonia) are required during fermentation of corncobs or cellulosic or lignocellulosic materials containing significant amounts of corncobs.

Corncobs, before and after comminution, are also easier to convey and disperse, and have a lesser tendency to form explosive mixtures in air than other cellulosic or lignocellulosic materials such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, and mixtures of any of these. For example paper products as described in U.S. application Ser. No. 13/396,365 filed Feb. 14, 2012 (US Pub. No. 2013-0052687, published Feb. 28, 2013), the full disclosure of which is incorporated herein by reference.

Cellulosic materials can also include lignocellulosic materials which have been de-lignified.

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems.

The biomass material can also include offal, and similar sources of material.

In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012 (US Pub. No. 2013-0052682, published Feb. 28, 2013), the full disclosure of which is incorporated herein by reference.

Any of the methods described herein can be practiced with mixtures of any biomass materials described herein.

Biomass Material Preparation—Mechanical Treatments

The biomass can be in a dry form, for example, with less than about 35% moisture content (e.g., less than about 20%, less than about 15%, less than about 10% less than about 5%, less than about 4%, less than about 3%, less than about 2% or even less than about 1%). The biomass can also be delivered in a wet state, for example as a wet solid, a slurry or a suspension with at least about 10 wt % solids (e.g., at least about 20 wt. %, at least about 30 wt. %, at least about 40 wt. %, at least about 50 wt. %, at least about 60 wt. %, at least about 70 wt. %).

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-treatment processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration the desired biomass falls through the perforations or screen and thus biomass larger than the perforations or screen are not irradiated. These larger materials can be re-processed, for example, by comminuting, or they can simply be removed from processing. In another configuration, material that is larger than the perforations is irradiated and the smaller material is removed by the screening process or recycled. In this kind of a configuration, the conveyor itself (for example, a part of the conveyor) can be perforated or made with a mesh. For example, in one particular embodiment the biomass material may be wet and the perforations or mesh allow water to drain away from the biomass before irradiation.

Screening of material can also be by a manual method, for example by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-treatment processing can include heating the material. For example a portion of the conveyor can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, $CO_2$, Argon) over and/or through the biomass as it is being conveyed.

Optionally, pre-treatment processing can include cooling the material. Cooling material is described in U.S. Pat. No. 7,900,857 to Medoff, the disclosure of which in incorporated herein by reference. For example, cooling can be by supplying a cooling fluid, for example water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-treatment processing method can include adding a material to the biomass. The additional material can be added by, for example, by showering, sprinkling and or pouring the material onto the biomass as it is conveyed. Materials that can be added include, for example, metals, ceramics and/or ions as described in U.S. Pat. App. Pub. 2010/0105119 A1 (filed Oct. 26, 2009 and published Apr. 29, 2010) and U.S. Pat. App. Pub. 2010/0159569 A1 (filed Dec. 16, 2009 and published Jun. 24, 2010), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be delivered to the conveyor by a belt conveyor, a pneumatic conveyor, a screw conveyor, a hopper, a pipe, manually or by a combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils of an electron gun (if such a device is used for treating the material).

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches.

Generally, it is preferred to convey the material as quickly as possible through the electron beam to maximize throughput. For example, the material can be conveyed at rates of at least 1 ft/min, e.g., at least 2 ft/min, at least 3 ft/min, at least 4 ft/min, at least 5 ft/min, at least 10 ft/min, at least 15 ft/min, 20, 25, 30, 35, 40, 45, 50 ft/min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through the radiation zone, optional post-treatment processing can be done. The optional post-treatment processing can, for example, be a process described with respect to the pre-irradiation processing. For example, the biomass can be screened, heated, cooled, and/or combined with additives. Uniquely to post-irradiation, quenching of the radicals can occur, for example, quenching of radicals by the addition of fluids or gases (e.g., oxygen, nitrous oxide, ammonia, liquids), using pressure, heat, and/or the addition of radical scavengers. For example, the biomass can be conveyed out of the enclosed conveyor and exposed to a gas (e.g., oxygen) where it is quenched, forming caboxylated groups. In one embodiment, the biomass is exposed during irradiation to the reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the biomass material. These processes can be applied before, during and or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the biomass material, increase the surface area of the biomass material and/or decrease one or more dimensions of the biomass material.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. For example, a feedstock material can be conveyed through ionizing radiation using a conveyor as described herein and then mechanically treated. Chemical treatment can remove some or all of the lignin (for example chemical pulping) and can partially or completely hydrolyze the material. The methods also can be used with pre-hydrolyzed material. The methods also can be used with material that has not been pre hydrolyzed The methods can be used with mixtures of hydrolyzed and non-hydrolyzed materials, for example with about 50% or more non-hydrolyzed material, with about 60% or more non-hydrolyzed material, with about 70% or more non-hydrolyzed material, with about 80% or more non-hydrolyzed material or even with 90% or more non-hydrolyzed material.

In addition to size reduction, which can be performed initially and/or later in processing, mechanical treatment can also be advantageous for opening up, stressing, breaking or shattering the biomass materials, making the cellulose of the materials more susceptible to chain scission and/or disruption of crystalline structure during the physical treatment.

Methods of mechanically treating the biomass material include, for example, milling or grinding. Milling may be performed using, for example, a mill, ball mill, colloid mill, conical or cone mill, disk mill, edge mill, Wiley mill, grist mill or other mill. Grinding may be performed using, for example, a cutting/impact type grinder. Some exemplary grinders include stone grinders, pin grinders, coffee grinders, and burr grinders. Grinding or milling may be provided, for example, by a reciprocating pin or other element, as is the case in a pin mill. Other mechanical treatment methods include mechanical ripping, tearing, shearing or chopping, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 (which was filed Oct. 26, 2007, and published Jun. 19, 2008), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source.

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated biomass materials, are described in further detail in U.S. Pat. App. Pub. 2012/0100577 A1, filed Oct. 18, 2011, and published Apr. 26, 2012, the full disclosure of which is hereby incorporated herein by reference.

Treatment of Biomass Material—Particle Bombardment

One or more treatments with energetic particle bombardment can be used to process raw feedstock from a wide variety of different sources to extract useful substances from the feedstock, and to provide partially degraded organic material which functions as input to further processing steps and/or sequences. Particle bombardment can reduce the molecular weight and/or crystallinity of feedstock. In some embodiments, energy deposited in a material that releases an electron from its atomic orbital can be used to treat the materials. The bombardment may be provided by heavy charged particles (such as alpha particles or protons), electrons (produced, for example, in beta decay or electron beam accelerators), or electromagnetic radiation (for example, gamma rays, x rays, or ultraviolet rays). Alternatively, radiation produced by radioactive substances can be used to treat the feedstock. Any combination, in any order, or concurrently of these treatments may be utilized. In another approach, electromagnetic radiation (e.g., produced using electron beam emitters) can be used to treat the feedstock.

Each form of energy ionizes the biomass via particular interactions. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 atomic units. Accelerators used to accelerate the particles can be electrostatic DC, electrodynamic DC, RF linear, magnetic induction linear or continuous wave. For example, cyclotron type accelerators are available from IBA (Ion Beam Accelerators, Louvain-la-Neuve, Belgium), such as the Rhodotron™ system, while DC type accelerators are available from RDI, now IBA Industrial, such as the Dynamitron™. Ions and ion accelerators are discussed in Introductory Nuclear Physics, Kenneth S. Krane, John Wiley & Sons, Inc. (1988), Krsto Prelec, FIZIKA B 6 (1997) 4, 177-206; Chu, William T., "Overview of Light-Ion Beam Therapy", Columbus-Ohio, ICRU-IAEA Meeting, 18-20 Mar. 2006; Iwata, Y. et al., "Alternating-Phase-Focused IH-DTL for Heavy-Ion Medical Accelerators", Proceedings of EPAC 2006, Edinburgh, Scotland; and Leitner, C. M. et al., "Status of the Superconducting ECR Ion Source Venus", Proceedings of EPAC 2000, Vienna, Austria.

The doses applied depend on the desired effect and the particular feedstock. For example, high doses can break chemical bonds within feedstock components and low doses can increase chemical bonding (e.g., cross-linking) within feedstock components.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when oxygen-containing functional groups are desired, treatment in the presence of oxygen or even treatment with oxygen ions can be performed. For example, when nitrogen-containing functional groups are desirable, treatment in the presence of nitrogen or even treatment with nitrogen ions can be performed.

Other Forms of Energy

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient.

Electromagnetic radiation is subclassified as gamma rays, x rays, ultraviolet rays, infrared rays, microwaves, or radiowaves, depending on the wavelength.

For example, gamma radiation can be employed to treat the materials. Gamma radiation has the advantage of a significant penetration depth into a variety of material in the sample. Sources of gamma rays include radioactive nuclei, such as isotopes of cobalt, calcium, technetium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Various other devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 B2, the complete disclosure of which is incorporated herein by reference.

Treatment of Biomass Material—Electron Bombardment

The feedstock may be treated with electron bombardment to modify its structure and thereby reduce its recalcitrance. Such treatment may, for example, reduce the average molecular weight of the feedstock, change the crystalline structure of the feedstock, and/or increase the surface area and/or porosity of the feedstock.

Electron bombardment via an electron beam is generally preferred, because it provides very high throughput and because the use of a relatively low voltage/high power electron beam device eliminates the need for expensive concrete vault shielding, as such devices are "self-shielded" and provide a safe, efficient process. While the "self-shielded" devices do include shielding (e.g., metal plate shielding), they do not require the construction of a concrete vault, greatly reducing capital expenditure and often allowing an existing manufacturing facility to be used without expensive modification. Electron beam accelerators are available, for example, from IBA (Ion Beam Applications, Louvain-la-Neuve, Belgium), Titan Corporation (San Diego, Calif., USA), and NHV Corporation (Nippon High Voltage, Japan).

Electron bombardment may be performed using an electron beam device that has a nominal energy of less than 10 MeV, e.g., less than 7 MeV, less than 5 MeV, or less than 2 MeV, e.g., from about 0.5 to 1.5 MeV, from about 0.8 to 1.8 MeV, from about 0.7 to 1 MeV, or from about 1 to 3 MeV. In some implementations the nominal energy is about 500 to 800 keV.

The electron beam may have a relatively high total beam power (the combined beam power of all accelerating heads, or, if multiple accelerators are used, of all accelerators and all heads), e.g., at least 25 kW, e.g., at least 30, 40, 50, 60, 65, 70, 80, 100, 125, or 150 kW. In some cases, the power is even as high as 500 kW, 750 kW, or even 1000 kW or more. In some cases the electron beam has a beam power of 1200 kW or more.

This high total beam power is usually achieved by utilizing multiple accelerating heads. For example, the electron beam device may include two, four, or more accelerating heads. The use of multiple heads, each of which has a relatively low beam power, prevents excessive temperature rise in the material, thereby preventing burning of the material, and also increases the uniformity of the dose through the thickness of the layer of material.

In some implementations, it is desirable to cool the material during electron bombardment. For example, the material can be cooled while it is being conveyed, for example, by a screw extruder or other conveying equipment.

To reduce the energy required by the recalcitrance-reducing process, it is desirable to treat the material as quickly as possible. In general, it is preferred that treatment be performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 2 Mrad per second. Higher dose rates generally require higher line speeds, to avoid thermal decomposition of the material. In one implementation, the accelerator is set for 3 MeV, 50 mAmp beam current, and the line speed is 24 feet/minute, for a sample thickness of about 20 mm (e.g., comminuted corn cob material with a bulk density of 0.5 g/cm$^3$).

In some embodiments, electron bombardment is performed until the material receives a total dose of at least 0.5 Mrad, e.g., at least 5, 10, 20, 30 or at least 40 Mrad. In some embodiments, the treatment is performed until the material receives a dose of from about 0.5 Mrad to about 150 Mrad, about 1 Mrad to about 100 Mrad, about 2 Mrad to about 75 Mrad, 10 Mrad to about 50 Mrad, e.g., about 5 Mrad to about 50 Mrad, from about 20 Mrad to about 40 Mrad, about 10 Mrad to about 35 Mrad, or from about 25 Mrad to about 30 Mrad. In some implementations, a total dose of 25 to 35 Mrad is preferred, applied ideally over a couple of seconds, e.g., at 5 Mrad/pass with each pass being applied for about one second. Applying a dose of greater than 7 to 8 Mrad/pass can in some cases cause thermal degradation of the feedstock material.

Using multiple heads as discussed above, the material can be treated in multiple passes, for example, two passes at 10 to 20 Mrad/pass, e.g., 12 to 18 Mrad/pass, separated by a few seconds of cool-down, or three passes of 7 to 12 Mrad/pass, e.g., 9 to 11 Mrad/pass. As discussed above, treating the material with several relatively low doses, rather than one high dose, tends to prevent overheating of the material and also increases dose uniformity through the thickness of the material. In some implementations, the material is stirred or otherwise mixed during or after each pass and then smoothed into a uniform layer again before the next pass, to further enhance treatment uniformity.

In some embodiments, electrons are accelerated to, for example, a speed of greater than 75 percent of the speed of light, e.g., greater than 85, 90, 95, or 99 percent of the speed of light.

In some embodiments, any processing described herein occurs on lignocellulosic material that remains dry as acquired or that has been dried, e.g., using heat and/or reduced pressure. For example, in some embodiments, the cellulosic and/or lignocellulosic material has less than about five percent by weight retained water, measured at 25° C. and at fifty percent relative humidity.

Electron bombardment can be applied while the cellulosic and/or lignocellulosic material is exposed to air, oxygen-enriched air, or even oxygen itself, or blanketed by an inert gas such as nitrogen, argon, or helium. When maximum oxidation is desired, an oxidizing environment is utilized, such as air or oxygen and the distance from the beam source is optimized to maximize reactive gas formation, e.g., ozone and/or oxides of nitrogen.

In some embodiments, two or more electron sources are used, such as two or more ionizing sources. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light. The biomass is conveyed through the treatment zone where it can be bombarded with electrons. It is generally preferred that the bed of biomass material has a relatively uniform thickness, as previously described, while being treated.

It may be advantageous to repeat the treatment to more thoroughly reduce the recalcitrance of the biomass and/or further modify the biomass. In particular the process parameters can be adjusted after a first (e.g., second, third, fourth or more) pass depending on the recalcitrance of the material. In some embodiments, a conveyor can be used which includes a circular system where the biomass is conveyed multiple times through the various processes described above. In some other embodiments multiple treatment devices (e.g., electron beam generators) are used to treat the biomass multiple (e.g., 2, 3, 4 or more) times. In yet other embodiments, a single electron beam generator may be the source of multiple beams (e.g., 2, 3, 4 or more beams) that can be used for treatment of the biomass.

The effectiveness in changing the molecular/supermolecular structure and/or reducing the recalcitrance of the biomass depends on the electron energy used and the dose applied, while exposure time depends on the power and dose.

In some embodiments, the treatment (with any electron source or a combination of sources) is performed until the material receives a dose of at least about 0.05 Mrad, e.g., at least about 0.1, 0.25, 0.5, 0.75, 1.0, 2.5, 5.0, 7.5, 10.0, 15, 20, 25, 30, 40, 50, 60, 70, 80, 90, 100, 125, 150, 175, or 200 Mrad. In some embodiments, the treatment is performed until the material receives a dose of between 0.1-100 Mrad, 1-200, 5-200, 10-200, 5-150, 5-100, 5-50, 5-40, 10-50, 10-75, 15-50, 20-35 Mrad.

In some embodiments, the treatment is performed at a dose rate of between 5.0 and 1500.0 kilorads/hour, e.g., between 10.0 and 750.0 kilorads/hour or between 50.0 and 350.0 kilorads/hours. In other embodiments the treatment is performed at a dose rate of between 10 and 10000 kilorads/hr, between 100 and 1000 kilorad/hr, or between 500 and 1000 kilorads/hr.

Electron Sources

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, accelerates them through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scans them magnetically in the x-y plane, where the electrons are initially accelerated in the z direction down the tube and extracted through a foil window. Scanning the electron beam is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 to Medoff, the complete disclosure of which is incorporated herein by reference.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of biomass materials, for example, by the mechanism of chain scission. In addition, electrons having energies of 0.5-10 MeV can penetrate low density materials, such as the biomass materials described herein, e.g., materials having a bulk density of less than 0.5 g/cm$^3$, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV. Methods of irradiating materials are discussed in U.S. Pat. App. Pub. 2012/0100577 A1, filed Oct. 18, 2011, and published Apr. 26, 2012, the entire disclosure of which is herein incorporated by reference.

Electron beam irradiation devices may be procured commercially from Ion Beam Applications (Louvain-la-Neuve, Belgium), the Titan Corporation (San Diego, Calif., USA), and NHV Corporation (Nippon High Voltage, Japan). Typical electron energies can be 0.5 MeV, 1 MeV, 2 MeV, 4.5 MeV, 7.5 MeV, or 10 MeV. Typical electron beam irradiation device power can be 1 KW, 5 KW, 10 KW, 20 KW, 50 KW, 60 KW, 70 KW, 80 KW, 90 KW, 100 KW, 125 KW, 150 KW, 175 KW, 200 KW, 250 KW, 300 KW, 350 KW, 400 KW, 450 KW, 500 KW, 600 KW, 700 KW, 800 KW, 900 KW or even 1000 KW.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam is preferred in most embodiments describe herein because of the larger scan width and reduced possibility of local heating and failure of the windows.

Treatment of Biomass Material—Sonication, Pyrolysis, Oxidation, Steam Explosion

If desired, one or more sonication, pyrolysis, oxidative, or steam explosion processes can be used in addition to or instead of other treatments to further reduce the recalcitrance of the biomass material. These processes can be applied before, during and/or after another treatment or treatments. These processes are described in detail in U.S. Pat. No. 7,932,065 to Medoff, the full disclosure of which is incorporated herein by reference.

Use of Treated Biomass Material

Using the methods described herein, a starting biomass material (e.g., plant biomass, animal biomass, paper, and municipal waste biomass) can be used as feedstock to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Intermediates and Products

Using the processes described herein, the biomass material can be converted to one or more products, such as energy, fuels, foods and materials. Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols and polyols (e.g., glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, and polyglycitol and other polyols), and methyl or ethyl esters of any of these alcohols. Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

Any combination of the above products with each other, and/or of the above products with other products, which other products may be made by the processes described herein or otherwise, may be packaged together and sold as products. The products may be combined, e.g., mixed, blended or co-dissolved, or may simply be packaged or sold together.

Any of the products or combinations of products described herein may be sanitized or sterilized prior to selling the products, e.g., after purification or isolation or even after packaging, to neutralize one or more potentially undesirable contaminants that could be present in the product(s). Such sanitation can be done with electron bombardment, for example, be at a dosage of less than about 20 Mrad, e.g., from about 0.1 to 15 Mrad, from about 0.5 to 7 Mrad, or from about 1 to 3 Mrad.

The processes described herein can produce various by-product streams useful for generating steam and electricity to be used in other parts of the plant (co-generation) or sold on the open market. For example, steam generated from burning by-product streams can be used in a distillation process. As another example, electricity generated from burning by-product streams can be used to power electron beam generators used in pretreatment.

The by-products used to generate steam and electricity are derived from a number of sources throughout the process. For example, anaerobic digestion of wastewater can produce a biogas high in methane and a small amount of waste biomass (sludge). As another example, post-saccharification and/or post-distillate solids (e.g., unconverted lignin, cellulose, and hemicellulose remaining from the pretreatment and primary processes) can be used, e.g., burned, as a fuel.

Many of the products obtained, such as ethanol or n-butanol, can be utilized as a fuel for powering cars, trucks, tractors, ships or trains, e.g., as an internal combustion fuel or as a fuel cell feedstock. Many of the products obtained can also be utilized to power aircraft, such as planes, e.g., having jet engines or helicopters. In addition, the products described herein can be utilized for electrical power generation, e.g., in a conventional steam generating plant or in a fuel cell plant.

Other intermediates and products, including food and pharmaceutical products, are described in U.S. Pat. App. Pub. 2010/0124583 A1, published May 20, 2010, to Medoff, the full disclosure of which is hereby incorporated by reference herein.

Saccharification

The treated biomass materials can be saccharified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the biomass material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published in English as WO 2010/135380 Nov. 25, 2010, and designated the United States, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40% by weight, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the biomass material with the enzyme. The concentration can be controlled, e.g., by controlling how much saccharification takes place. For example, concentration can be increased by adding more biomass material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

Saccharifying Agents

Suitable cellulolytic enzymes include cellulases from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum*, and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additional strains that can be used include, but are not limited to, *Trichoderma* (particularly *T. viride, T. reesei*, and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

Many microorganisms that can be used to saccharify biomass material and produce sugars can also be used to ferment and convert those sugars to useful products.

Sugars

In the processes described herein, for example, after saccharification, sugars (e.g., glucose and xylose) can be isolated. For example, sugars can be isolated by precipitation, crystallization, chromatography (e.g., simulated moving bed chromatography, high pressure chromatography), centrifugation, extraction, any other isolation method known in the art, and combinations thereof.

Hydrogenation and Other Chemical Transformations

The processes described herein can include hydrogenation. For example, glucose and xylose can be hydrogenated to sorbitol and xylitol respectively. Hydrogenation can be accomplished by use of a catalyst (e.g., Pt/gamma-$Al_2O_3$, Ru/C, Raney Nickel, or other catalysts know in the art) in combination with $H_2$ under high pressure (e.g., 10 to 12000 psi). Other types of chemical transformation of the products from the processes described herein can be used, for example production of organic sugar derived products such (e.g., furfural and furfural-derived products). Chemical transformations of sugar derived products are described in U.S. Prov. App. No. 61/667,481, filed Jul. 3, 2012, the disclosure of which is incorporated herein by reference in its entirety.

Fermentation

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic condition, can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance.

Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub. 2012/0052536, filed Jul. 15, 2011, published Mar. 1, 2012, the complete disclosure of which is incorporated herein by reference.

"Fermentation" includes the methods and products that are disclosed in U.S. Prov. App. No. 61/579,559, filed Dec. 22, 2012, and U.S. Prov. App. No. 61/579,576, filed Dec. 22, 2012, the contents of both of which are incorporated by reference herein in their entirety.

Mobile fermenters can be utilized, as described in International App. No. PCT/US2007/074028 (which was filed Jul. 20, 2007, was published as WO 2008/011598 on Jan. 24, 2008), the contents of which is incorporated herein in its entirety. Similarly, the saccharification equipment can be mobile. Further, saccharification and/or fermentation may be performed in part or entirely during transit.

Fermentation Agents

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protist (including, but not limited to, e.g., a slime mold), or an alga. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. saccharobutylicum, C. Puniceum, C. beijernckii*, and *C. acetobutylicum*), *Moniliella pollinis, Moniliella megachiliensis, Lactobacillus* spp. *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula*.

For instance, *Clostridium* spp. can be used to produce ethanol, butanol, butyric acid, acetic acid, and acetone. *Lactobacillus* spp., can be used to produce lactic acid.

Many such microbial strains are publicly available, either commercially or through depositories such as the ATCC (American Type Culture Collection, Manassas, Va., USA), the NRRL (Agricultural Research Sevice Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Many microorganisms that can be used to saccharify biomass material and produce sugars can also be used to ferment and convert those sugars to useful products.

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing a saccharified product, the method comprising:
   providing
      a reduced-recalcitrance cellulosic or lignocellulosic biomass disposed within a first structure or carrier and
      a microorganism and a liquid medium disposed within a second carrier or structure,
   wherein the first structure or carrier is formed of a mesh material having a maximum opening size of less than 1 mm and is disposed within the second carrier or structure, under conditions that allow the passage of a molecule of the cellulosic or lignocellulosic biomass out of and/or into the first structure or carrier, and
   allowing an enzyme of the microorganism to saccharify the molecule to the product.

2. The method of claim 1, wherein the microorganism comprises a strain of *Trichoderma reesei*.

3. The method of claim 2, wherein the strain is a high-yielding cellulase-producing mutant of *Trichoderma reesei*.

4. The method of claim 3, wherein the strain comprises *T. reesei* RUT-C30.

5. The method of claim 1, where the first structure or carrier is made of a bioerodible polymer.

6. The method of claim 5, where the bioerodible polymer is selected from the group consisting of: polylactic acid, polyhydroxybutyrate, polyhydroxyalkanoate, polyhydroxybutyrate-valerate, polycaprolactone, polyhydroxybutyrate-hexanoate, polybutylene succinate, polybutyrate succinate adipate, polyesteramide, polybutylene adipate-co-terephthalate, mixtures thereof, and laminates thereof.

7. The method of claim 5, wherein the first structure or carrier is made of a starch film.

8. The method of claim 1, where the recalcitrance of the cellulosic or lignocellulosic material has been reduced by a treatment method selected from the group consisting of: bombardment with electrons, sonication, oxidation, pyrolysis, steam explosion, chemical treatment, mechanical treatment, freeze grinding and combinations thereof.

9. The method of claim 1, wherein the recalcitrance of the cellulosic or lignocellulosic biomass has been reduced by exposure to an electron beam.

10. The method of claim 1, wherein the cellulosic or lignocellulosic biomass is selected from the group consisting of: paper, paper products, paper waste, paper pulp, pigmented papers, loaded papers, coated papers, filled papers, magazines, printed matter, printer paper, polycoated paper, card stock, cardboard, paperboard, cotton, wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, offal, agricultural or industrial waste, arracacha, buckwheat, banana, barley, cassava, kudzu, oca, sago, sorghum, potato, sweet potato, taro, yams, beans, favas, lentils, peas, and mixtures of any of these.

11. The method of claim 10, wherein the cellulosic or lignocellulosic biomass comprises corn cobs.

12. A method for producing a saccharified product, the method comprising:
   providing
      a reduced-recalcitrance cellulosic or lignocellulosic biomass disposed within a first structure or carrier and
      a microorganism and a liquid medium disposed within a second carrier or structure,
   wherein the first structure or carrier is made of a bioerodible polymer and is disposed within the second carrier or structure, under conditions that allow the passage of a molecule of the cellulosic or lignocellulosic biomass out of and/or into the first structure or carrier, and allowing an enzyme of the microorganism to saccharify the molecule to the product.

13. The method of claim 12, wherein the microorganism comprises a strain of *Trichoderma reesei*.

14. The method of claim 13, wherein the strain is a high-yielding cellulase-producing mutant of *Trichoderma reesei*.

15. The method of claim 14, wherein the strain comprises *T. reesei* RUT-C30.

16. The method of claim 12, wherein the first structure or carrier is formed of a mesh material having a maximum opening size of less than 1 mm.

17. The method of claim 12, where the bioerodible polymer is selected from the group consisting of: polylactic acid, polyhydroxybutyrate, polyhydroxyalkanoate, polyhydroxybutyrate-valerate, polycaprolactone, polyhydroxybutyrate-hexanoate, polybutylene succinate, polybutyrate succinate adipate, polyesteramide, polybutylene adipate-co-terephthalate, mixtures thereof, and laminates thereof.

18. The method of claim 12, wherein the first structure or carrier is made of a starch film.

19. The method of claim 12, where the recalcitrance of the cellulosic or lignocellulosic material has been reduced by a treatment method selected from the group consisting of: bombardment with electrons, sonication, oxidation, pyrolysis, steam explosion, chemical treatment, mechanical treatment, freeze grinding and combinations thereof.

20. The method of claim 12, wherein the recalcitrance of the cellulosic or lignocellulosic biomass has been reduced by exposure to an electron beam.

21. The method of claim 12, wherein the cellulosic or lignocellulosic biomass is selected from the group consisting of: paper, paper products, paper waste, paper pulp, pigmented papers, loaded papers, coated papers, filled papers, magazines, printed matter, printer paper, polycoated paper, card stock, cardboard, paperboard, cotton, wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, offal, agricultural or industrial waste, arracacha, buckwheat, banana, barley, cassava, kudzu, oca, sago, sorghum, potato, sweet potato, taro, yams, beans, favas, lentils, peas, and mixtures of any of these.

22. The method of claim 21, wherein the cellulosic or lignocellulosic biomass comprises corn cobs.

* * * * *